United States Patent [19]

Edwards et al.

[11] Patent Number: 4,866,072

[45] Date of Patent: Sep. 12, 1989

[54] METHOD OF TREATING CYSTIC FIBROSIS

[75] Inventors: Alan M. Edwards, Melton Mowbray, England; Richard A. Foulds, Stow, Mass.

[73] Assignee: Fisons plc, Ipswich, England

[21] Appl. No.: 157,715

[22] Filed: Feb. 18, 1988

[30] Foreign Application Priority Data

Feb. 21, 1987 [GB] United Kingdom ................ 8704089

[51] Int. Cl.$^4$ .............................................. A61K 31/44
[52] U.S. Cl. ...................................... 514/291; 514/851
[58] Field of Search ................................ 514/291, 851

[56] References Cited

U.S. PATENT DOCUMENTS

| | | | |
|---|---|---|---|
| 4,419,352 | 12/1983 | Cox et al. | 546/89 X |
| 4,698,345 | 10/1987 | Dicker et al. | 514/291 |
| 4,760,072 | 7/1988 | Brown et al. | 514/291 |

OTHER PUBLICATIONS

The Merck Manual, 14th ed., 1982, pp. 635–639.

Primary Examiner—Leonard Schenkman
Attorney, Agent, or Firm—Marshall, O'Toole, Gerstein, Murray & Bicknell

[57] ABSTRACT

A method of treatment of cystic fibrosis which comprises administration to a patient suffering from that condition of a therapeutically effective quantity of 9-ethyl-6,9-dihydro-4,6-dioxo-10-propyl-4H-pyrano(3,2-g)quinoline-2,8-dicarbo xylic acid or a pharmaceutically acceptable derivative thereof.

Pharmaceutically acceptable salts of the active ingredient which may be used include alkali metal salts, in particular the di-sodium salt which is known as nedocromil sodium.

10 Claims, No Drawings

METHOD OF TREATING CYSTIC FIBROSIS

METHOD OF TREATMENT

This invention relates to a new use of known pharmaceutical compounds, namely to the use of those compounds in the treatment of cystic fibrosis.

BACKGROUND TO THE INVENTION

Cystic fibrosis is an inherited multi-system disorder which is characterized by an abnormality in exocrine gland function and which occurs almost exclusively in populations of European origin. The incidence of the disease amongst white Americans, for instance, is between 1/1600 and 1/2000 live births. Amongst black Americans, on the other hand, the incidence is only about 1/17000. Although survival of cystic fibrosis patients has improved in recent years, the median survival is still only about 20 years despite intensive supportive and prophylactic treatment.

Cystic fibrosis is uniformly fatal. Nearly all patients suffering from the disease develop chronic progressive disease of the respiratory system, the most common cause of death being pulmonary disease. Also, in the majority of cases, pancreatic dysfunction occurs; hepatobiliary and genitourinary diseases are also frequent. It is thought that the primary defect of the condition is related to abnormalities of chloride and sodium transport across mucous membranes.

Nedocromil sodium, the disodium salt of 9-ethyl-6,9-dihydro-4,6-dioxo-10-propyl-4H-pyrano(3,2-g)quinoline-2,8-dicarboxylic acid, has been known for some time, eg from British Patent Application No 2157291A, for the treatment of reversible obstructive airways disease by administration as a pressurised aerosol. We have now surprisingly found that administration of 9-ethyl-6,9-dihydro-4,6-dioxo-10-propyl-4H-pyrano(3,2-g)quinoline-2,8-dicarboxylic acid or a pharmaceutically acceptable derivative thereof may be useful in the treatment of cystic fibrosis.

SUMMARY OF THE INVENTION

According to the invention there is provided a method of treatment of cystic fibrosis which comprises administration to a patient suffering from that condition of a therapeutically effective quantity of 9-ethyl-6,9-dihydro-4,6-dioxo-10-propyl-4H-pyrano(3,2-g)quinoline-2,8-dicarboxylic acid or a pharmaceutically acceptable derivative thereof.

DETAILED DESCRIPTION OF THE INVENTION

Pharmaceutically acceptable derivatives of the active ingredient include pharmaceutically acceptable metal ion salts, such as alkali metal salts, eg the di-sodium and di-potassium salts. We especially prefer the di-sodium salt, which is commonly known as nedocromil sodium.

Administration of the active ingredient is most commonly directly to the patient's lung, eg as a pressurised aerosol or as a nebulised solution. The latter mode of administration is preferred for the treatment of children, especially infants. Alternatively, administration may be by the oral route.

Solutions for administration by nebulisation are preferably aqueous solutions. The solution may contain from about 0.1 to 10% w/v of the active ingredient. However, we prefer the active ingredient to be present at a level of less than 2%, eg 0.5% or 1.0% w/v. The concentration of choice will of course depend on, among other factors, the severity of the disease.

In addition to the active ingredient the solution may contain a preservative. Preservatives which may be mentioned include quaternary ammonium compounds, in particular the mixture of alkyl benzyl dimethyl ammonium compounds known generically as 'Benzalkonium Chloride'. However, the preferred preservative is chlorbutol.

The solution may also contain other conventional excipients. For example, the solution may be made isotonic using a suitable tonicity agent eg sodium chloride.

The solution may be put up in unit dosage form, in which case preservatives may be incorporated, but are generally not necessary. Alternatively the solution may be put up in multi-dose form. In general it will be necessary to incorporate one or more preservatives into multi-dose solutions to ensure that the solution remains sterile after initial use.

For administration as a powdered aerosol, the active ingredient is preferably formulated with a liquified propellant medium which is preferably a gas at room temperature. The most suitable liquified propellants are the fluorinated and fluorochlorinated lower alkanes such as are sold under the Registered Trade Mark 'Freon'.

The composition may also contain a surface-active agent. The surface-active agent may be a liquid or solid non-ionic surface-active or may be a solid anionic surface-active agent.

The active ingredient is preferably finely divided, eg having a mass median diameter in the range 0.01 to 10 microns.

We prefer the composition to contain from 0.5 to 12%, more preferably from 0.5 to 10%, and most preferably from 0.5 to 5%, eg about 1 to 3.5% w/w of finely divided active ingredient.

Compositions suitable for oral administration include solid dosage forms, eg tablets, dragees and hard or soft capsules, and liquid dosage forms, eg syrups, suspensions or dispersions. Such compositions may be prepared by working the active ingredient up with suitable adjuvants or excipients. Examples of such adjuvants or excipients are:

For tablets and dragees: Binders, eg cellulosic materials such as microcrystalline cellulose and methyl cellulose; disintegrating agents, eg starches, particularly maize starches; stabilisers, eg against hydrolysis of the active ingredients; flavouring agents, eg sugars; fillers; stearates and inorganic diluents, eg talc.

For hard or soft capsules: Diluents, eg lactose; glidants, eg stearates; inorganic materials, eg silica or talc; stabilisers and dispersing agents.

For syrups, suspensions or dispersions: A liquid vehicle in which the active ingredients may be dissolved or suspended, eg water; and suspending agents, eg cellulose derivatives, gums, etc.

The dosage to be administered will of course vary with, amongst other factors, the particular active ingredient used, the method of administration and the severity of the disease. However, in general a dosage of from about 1 to 50 mg, more preferably 1 to 20 mg administered 1 to 8, preferably 2 to 6 and most preferably 2 to 4 times a day is found to be satisfactory. The preferred total daily dosage for adult patients is from about 10 to 100 mg, more preferably 10 to 50 mg. For children, especially infants, the recommended daily dosage may be at the lower end of this range or may be less than this.

In general, the treatment is continued for a period of several months or years, possibly throughout the patient's lifetime.

We claim:

1. A method of treatment of cystic fibrosis which comprises administration to a patient suffering from that condition of a therapeutically effective quantity of 9-ethyl-6,9-dihydro-4,6-dioxo-10-propyl-4H-pyrano(3,2-g)quinoline-2,8-dicarboxylic acid or a pharmaceutically acceptable derivative thereof.

2. A method according to claim 1, wherein the active ingredient is nedocromil sodium.

3. A method according to claim 1, wherein the active ingredient is administered directly to the patient's lung.

4. A method according to claim 3, wherein the active ingredient is administered as an aqueous solution.

5. A method according to claim 3, wherein the active ingredient is administered as an aqueous solution containing from 0.1 to 2% w/w of active ingredient.

6. A method according to claim 3, wherein the active ingredient is administered as a pressurised aerosol.

7. A method according to claim 3, wherein the active ingredient is administered as a pressurised aerosol containing from 0.5 to 5% w/w of active ingredient.

8. A method according to claim 1, wherein the active ingredient is administered orally.

9. A method according to claim 1, wherein the total daily dosage is from 10 to 100 mg of active ingredient.

10. A method according to claim 1, wherein the total daily dosage is from 10 to 50 mg of active ingredient.

* * * * *